United States Patent [19]

Prosen

[11] 4,229,215

[45] Oct. 21, 1980

[54] NON-PRECIOUS STAINLESS DENTAL ALLOY

[75] Inventor: Emil M. Prosen, Bala-Cynwyd, Pa.

[73] Assignee: Neoloy Products, Inc., Posen, Ill.

[21] Appl. No.: 51,003

[22] Filed: Jun. 22, 1979

[51] Int. Cl.² ............................................. C22C 19/07
[52] U.S. Cl. ..................................... 75/134 C; 75/171
[58] Field of Search ............................. 75/134 C, 171

[56] References Cited

U.S. PATENT DOCUMENTS 3,134,670  5/1964  Prosen .................................... 75/171

*Primary Examiner*—R. Dean

*Attorney, Agent, or Firm*—Jacobs & Jacobs

[57] ABSTRACT

The present invention provides a non-precious stainless dental alloy which may be used in producing crowns, bridges, inlays, and the like. It also provides an alloy which is especially adapted for the application of low fusing opaqueing porcelain for adhesion to such dental appliances. The alloy of the present invention has a melting point approximating 2550° F. In its broadest aspect the alloy consists of cobalt 49 to 59%, chromium 25 to 30%, tungsten 7 to 14%, gallium 2 to 6%, copper 1 to 3%, niobium 0.5 to 2%, silicon 0.5 to 2%, and iron 0.5 to 6%.

4 Claims, No Drawings

NON-PRECIOUS STAINLESS DENTAL ALLOY

The present invention relates to a non-precious stainless alloy especially adapted for use in the dental field for the preparation of crowns, bridges, inlays, and other dental prostheses to which it is desired to apply a porcelain surface. The principal advantage of the alloy of the present invention is that it provides an alloy to which a low-fusing porcelain can be adhered by fusion, with none of the disadvantages of heretofore known alloys.

It is also an economy alloy in that it does not contain any of the higher priced metals such as gold and platinum.

BACKGROUND OF THE INVENTION

In the dental field it is now well recognized that the alloy to which low-fusing porcelain can be successfully applied so as to have complete adhesion must be compatible from the standpoint of coefficient of linear expansion and contraction at the fusing temperature of the porcelain; and that such alloy must provide on its surface oxides which facilitate the adhesion of the porcelain.

It is also well understood that after application of the porcelain to the alloy, the porcelain surface should not check, crack or separate from the base alloy.

There are on the market today various opaque porcelains which are especially prepared and sold for application to dental alloys. The opaqueing materials of such opaque porcelains vary from one to the other and the basic ingredients of such opaque porcelains are not fully disclosed in any literature with which I am familiar.

Among the various opaqueing porcelains with which I am familiar is one offered for sale and sold by Dentsply International Inc. of York, Pennsylvania under the trademark BIOBOND. Another is offered and sold by Vita Zahnfabrik H. Rauter K.G., of Sackingen, Germany, under the trademark VITA.

I also know that there are other opaque porcelains sold under the trademark CERAMCO by Ceramco, Inc. of Long Island City, N.Y. and under the trademark HOWMEDICA by Howmedica, Inc. of New York, N.Y.

Essentially all of these opaque porcelains for dental application are said to be low fusing in that they will fuse at a temperature of about 1800° F. to dental alloys and will adhere to the same provided all other conditions are met for fusing such porcelains to the metal alloy.

SUMMARY OF THE INVENTION

According to the present invention, and after considerable experimental work, I have found that a non-precious stainless alloy consisting of the following elements in its preferred form can be fused to both BIOBOND and VITA opaque porcelains with excellent results. The preferred formulation for such an alloy is:

| Cobalt | 52% |
| --- | --- |
| Chromium | 28% |
| Tungsten | 12% |
| Gallium | 4% |
| Copper | 1% |
| Niobium | 1% |
| Silicon | 0.5% |
| Iron | 1.5% |

According to laboratory tests which I have conducted and which I have also had made by an outside consulting laboratory, I can state that an alloy of this preferred formulation has the following mechanical characteristics:

| Melting Point | 2550° F. |
| --- | --- |
| Thermal coefficient of expansion measured between room temperature and 700° C. | $1.49 \times 10^{-5}$ per °C. |
| Yield Strength | 0.0021 |
| Tensile Strength kg/cm² (psi) | 7800 (111 000) |
| Elongation | 9% plus* |
| Averaged 30N Hardness | 48 |

*NOTE:
During the test by the consulting laboratory the ultra-high sensitivity strain gage necessary to measure the yield strength parameter had a maximum allowable elongation range of approximately 9%. At this point the gage had to be removed or else it would break. Hence the elongation of the alloy was in excess of 9%.

The specimen was tested by the outside laboratory according to ADA Specification 14.

DESCRIPTION OF THE INVENTION

Supplementing what is set forth under the foregoing heading of "Summary of The Invention", I have found that an alloy prepared according to the preferred formulation set forth, is ideally suited for fusing at approximately 1800° F. with opaque porcelain such as BIOBOND and VITA, and that, after fusing and cooling, such porcelains are so adherent to the alloy that it is impossible to separate the same under repeated hammer blows.

It is my firm belief from considerable experimental work in this area that the elements gallium, copper, niobium, silicon and iron, which are only added in small quantities to the basic alloy of cobalt, chromium and tungsten, contribute totally to the porcelain adhesive characteristics imparted to the alloy, and that without such additives insufficient oxides would be formed on the surface of such alloy.

I have found, and I believe it is well supported in the art, that surface oxides must be formed on the alloy in order to promote and assure adhesion by fusion of the opaque porcelain. In my experimentation I have determined that to provide such surface oxides for adhesion purposes, copper and niobium are essential in the small percentages set forth. Niobium provides an oxide which is almost part of the alloy and which is not readily removed by fluxing of the porcelain. Iron and niobium when combined form a very durable oxide.

In the broader aspect of the invention, I have found that the various elements constituting the alloy of the present invention may vary within the following ranges:

| Cobalt | 49 to 59% |
| --- | --- |
| Chromium | 25 to 30% |
| Tungsten | 7 to 14% |
| Gallium | 2 to 6% |
| Copper | 1 to 3% |
| Niobium | 0.5 to 2% |
| Silicon | 0.5 to 2% |
| Iron | 0.5 to 6% |

Within these ranges the three principal elements of cobalt, chromium and tungsten must be so proportioned as to assure that the coefficient of expansion and contraction of the alloy is suitable for porcelain application. Such coefficient of expansion must be approximately $1.4 \times 10^{-5}$ per °C. It can be slightly higher or slightly lower. The desired coefficient of expansion is accomplished by increasing the amount of chromium and tungsten and reducing the amount of cobalt.

It should also be noted that the amounts of copper, niobium, silicon and iron which chiefly provide the oxides for porcelain application, are limited to very minor ranges. Of these elements, copper and niobium are most important. Niobium oxide is not readily removed by fluxing. Increased amounts of iron provide greater adhesion.

Concerning gallium, I have found that this element, which not only promotes the formation of surface oxides, serves two additional purposes, i.e., it reduces the melting temperature of the alloy, and also contributes to its liquidity on melting.

What I claim is:

1. A stainless dental alloy especially adapted for the adhesion of opaqueing porcelain having a fusing temperature of approximately 1800° F., consisting essentially of:

| | |
|---|---|
| Cobalt | 49 to 59% |
| Chromium | 25 to 30% |
| Tungsten | 7 to 14% |
| Gallium | 2 to 6% |
| Copper | 1 to 3% |
| Niobium | 0.5 to 2% |
| Silicon | 0.5 to 2% |
| Iron | 0.5 to 6% | said alloy having a melting temperature of approximately 2550° F., and a linear coefficient of expansion of about $1.4 \times 10^{-5}$ per °C.

2. A stainless dental alloy according to claim 1, wherein the percentages of cobalt, chromium and tungsten are varied within the limits set forth to produce the melting temperature of approximately 2550° F.

3. A stainless dental alloy consisting essentially of:

| | |
|---|---|
| Cobalt | 52% |
| Chromium | 28% |
| Tungsten | 12% |
| Gallium | 4% |
| Copper | 1% |
| Niobium | 1% |
| Silicon | 0.5% |
| Iron | 1.5% |

4. A stainless dental alloy according to claim 3, especially adapted for adhesion to opaqueing porcelain having a fusing temperature of approximately 1800° F., said dental alloy having a melting temperature of approximately 2550° F. and a linear coefficient of expansion of approximately $1.4 \times 10^{-5}$ per °C.

* * * * *